(12) United States Patent  
Kim et al.

(10) Patent No.: US 7,740,877 B2
(45) Date of Patent: Jun. 22, 2010

(54) ALIPHATICALLY MODIFIED BIODEGRADABLE BLOCK COPOLYMERS AS THERMOGELLING POLYMERS

(75) Inventors: Sung Wan Kim, Salt Lake City, UT (US); Seongbong Jo, Salt Lake City, UT (US); Jin Kim, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 377 days.

(21) Appl. No.: 11/784,528

(22) Filed: Apr. 6, 2007

(65) Prior Publication Data

US 2007/0265356 A1 Nov. 15, 2007

Related U.S. Application Data

(60) Provisional application No. 60/790,179, filed on Apr. 7, 2006.

(51) Int. Cl.
*A61F 2/02* (2006.01)
*C08G 63/08* (2006.01)

(52) U.S. Cl. ........................ 424/426; 528/354
(58) Field of Classification Search ........................ None
See application file for complete search history.

(56) References Cited

U.S. PATENT DOCUMENTS 6,004,573 A 12/1999 Rathi et al.
6,117,949 A 9/2000 Rathi et al.
6,201,072 B1 3/2001 Rathi et al.

OTHER PUBLICATIONS

Jin Kon Kim et al The Aromatic Hydrocarbon resins with various Hydrogenation Degrees Part 1. The phase behavior with polybutadiene and polystyrene., Dept of Chemical Engineering and Polymer research Institute, Electric And COmputer Engineering Division, Pohang University of Science and technology Mar. 27, 2000.*

* cited by examiner

*Primary Examiner*—Carlos A Azpuru
(74) *Attorney, Agent, or Firm*—Clayton, Howarth & Cannon, P.C.

(57) ABSTRACT

A thermogelling, aliphatically modified polymer for use in drug delivery is described. Illustrative embodiments include poly(lactic-co-ε-caprolactone)-poly(ethylene glycol)-poly(lactic-co-ε-caprolactone) hexanoate and poly(lactic-co-ε-caprolactone)-poly(ethylene glycol)-poly(lactic-co-ε-caprolactone) laurate. Another illustrative embodiment includes a composition having a thermogelling amount of an aliphatically modified poly(lactic-co-ε-caprolactone)-poly(ethylene glycol)-poly(lactic-co-ε-caprolactone) and an effective amount of a drug. The thermogelling polymers are made by bonding an aliphatic group to poly(lactic-co-ε-caprolactone)-poly(ethylene glycol)-poly(lactic-co-ε-caprolactone). A method of use includes injecting a warm-blooded individual with a thermogelling amount of the aliphatically modified polymer and a drug.

19 Claims, 4 Drawing Sheets

ALIPHATICALLY MODIFIED BIODEGRADABLE BLOCK COPOLYMERS AS THERMOGELLING POLYMERS

CROSS-REFERENCE TO RELATED APPLICATIONS

This application claims the benefit of U.S. Provisional Application No. 60/790,179, filed Apr. 7, 2006, which is hereby incorporated by reference in its entirety.

STATEMENT REGARDING FEDERALLY SPONSORED RESEARCH OR DEVELOPMENT

Not applicable.

BACKGROUND OF THE INVENTION

This invention relates to drug delivery. More particularly, this invention relates to biodegradable tri-block copolymers that undergo reverse thermal gelation at about 30° C. That is, these polymers undergo a sol-to-gel transition as their temperature is raised from room temperature to body temperature. Thus, polymer solutions can be injected into an individual, and the solutions then undergo a transition to a gel, thereby forming a depot from which a drug can be released over time.

Biodegradable thermoreversible polymers in aqueous solutions that undergo the sol-to-gel phase transition upon temperature changes have been developed for their applications as delivery systems for drugs, cells, proteins, and genes. Jeong, B.; Bae, Y. H.; Lee, D. S.; Kim, S. W. *Nature* 1997, 388, 860-862; Rathi, R.; Zentner, G. M. U.S. Pat. No. 5,702,717, 1999; Zentner, G. M.; Rathi, R.; Shih, C.; McRea, J. C.; Seo, M.-H.; Oh, H.; Rhee, B. G.; Mestecky, J.; Moldoveanu, Z.; Morgan, M. *J. Controlled Release* 2001, 72, 203-215; Li, Z.; Ning, W.; Wang, J.; Choi, A.; Lee, P.-Y.; Tyagi, P.; Huang, L. *Pharm. Res.* 2003, 20, (6), 884-888. Such biodegradable thermoreversible polymers have typically been engineered from hydrophilic poly(ethylene glycol) block(s) and hydrophobic biodegradable block(s). With an exquisite balance of hydrophilicity and hydrophobicity, aqueous solutions of the engineered polymers have undergone the unique phase transition at below body temperature. Zentner et al., supra; Shim, M. S.; Lee, H. T.; Shim, W. S.; Park, I.; Lee, H.; Chang, T.; Kim, S. W.; Lee, D. S. *J. Biomed. Mater. Res.* 2002, 61, (2), 188-196; Jeong, B.; Bae, Y. H.; Kim, S. W. *Macromolecules* 1999, 32, 7064-7069. This unique gelation of the polymers has been considered useful for their applications for the formulation of sensitive macromolecular therapeutics, as well as for small molecular drugs, because a mild temperature rise upon injection results in polymeric gel depots in vivo, which can control drug release.

In early work on thermogelling biodegradable polymers, Jeong et al. synthesized di- and tri-block copolymers of PEG and poly(lactide-co-glycolide) (PLGA) to develop polymeric gels, which were suggested to find applications as injectable drug delivery systems. Jeong, B.; Bae, Y. H.; Lee, D. S.; Kim, S. W. *Nature* 1997, 388, 860-862. Later, the use of low molecular weight PEG led to thermogelling polymers that uniquely undergo gelation upon a temperature rise. Zentner et al., supra; Shim et al., supra; Jeong, B.; Bae, Y. H.; Kim, S. W. *Macromolecules* 1999, 32, 7064-7069. Thermogelling properties of the tri-block copolymers synthesized from PEG and PLGA were affected by the chemical structure, concentration, and hydrophobic block length of the block copolymers. Thermogelling polymers with longer hydrophobic biodegradable PLGA blocks usually underwent gelation at lower temperatures than the polymers with shorter hydrophobic blocks. Shim et al., supra; Lee, D. S.; Shim, M. S.; Kim, S. W.; Lee, H.; Park, I.; Chang, T. *Macromol. Rapid Commun.* 2001, 22, 587-592. It is also interesting to note that thermogelling PLGA-PEG-PLGA (BAB) polymers gelled at lower concentrations than PEG-PLGA-PEG (ABA) polymers, although overall block lengths of the polymers were similar. The effects of monomer ratio and PEG molecular weight on thermal gelation of block copolymers were also systematically investigated. Shim et al., supra. Polymers that are applicable to drug delivery could be synthesized from low-molecular weight PEG (MW less than 2000). Even though PLGA-PEG-PLGA tri-block copolymers have shown excellent biocompatibility, Youxin, L.; Kissel, T. *J. Controlled Release* 1993, 27, (3), 247-257; Zange, R.; Li, Y.; Kissel, T. *J. Controlled Release* 1998, 56, 249-258, biodegradation and biocompatibility of the gel depot formed from thermogelling polymers with the same structure have been assessed after in vivo injection of a polymeric solution. Depending on the polymer structure and the block lengths of polymers, polymeric depots from thermoreversible polymers that were synthesized from PEG, lactide, and glycolide could last for up to 1 month without any noticeable indications of toxicity. Zentner et al., supra.

In addition to linear block copolymers, graft copolymers (PEG-g-PLGA) have been synthesized from PEG-diglycidyl ether, lactide, and glycolide. Jeong, B.; Wang, L.-Q.; Gutowska, A. *Chem. Commun.* 2001, 16, 1516-1517; Jeong, B.; Kibbey, M. R.; Birnbaum, J. C.; Won, Y.-Y.; Gutowska, A. *Macromolecules* 2000, 33, 8317-8322; Chung, Y.-M.; Simmons, K. L.; Gutowska, A.; Jeong, B. *Biomacromolecules* 2002, 3, 511-516. The PEG-g-PLGA polymers have also been reported to possess reverse thermogelling properties. Biodegradable blocks could also be prepared from monomers other than lactide and glycolide for thermogelling polymers. Caprolactone, which can be polymerized by ring-opening polymerization, has been successfully used for the preparation of thermogelling polymers of ABA and BAB structures. Hwang, M. J.; Suh, J. M.; Bae, Y. H.; Kim, S. W.; Jeong, B. *Biomacromolecules* 2005, 6, 885-890; Bae, S. J.; Suh, J. M.; Sohn, Y. S.; Bae, Y. H.; Kim, S. W.; Jeong, B. *Macromolecules* 2005, 38, 5260-5265. Caprolactone-based thermogelling polymers have been claimed to be advantageous for handling and reconstitution of polymers for practical applications as drug delivery systems. Biodegradable polyphosphazene or poly(propylene fumarate) blocks have also been utilized for the synthesis of thermogelling systems. Lee, B. H.; Lee, Y. M.; Sohn, Y. S.; Song, S.-C. *Macromolecules* 2002, 35, 3876-3879; Behravesh, E.; K. Shung, A.; Jo, S.; Mikos, A. G. *Biomacromolecules* 2002, 3, 153-158.

Thermogelling polymers synthesized from PEG and PLGA have been studied for their applications as drug delivery platforms. GLP-1 (glucagon-like peptide-1) and insulin have been formulated and delivered with thermogelling PLGA-PEG-PLGA polymers. Kwon, Y. M.; Kim, S. W. *Pharm. Res.* 2004, 21, (2), 339-343; Choi, S.; Baudys, M.; Kim, S. W. *Pharm. Res.* 2004, 21, (5), 821-31. In vivo studies using rats have shown that thermally formed polymeric depots from the PLGA-PEG-PLGA block copolymer extended the release of the proteins up to 10 days. In addition to proteins, small drug molecules, such as paclitaxel, have been successfully delivered by means of minimally invasive subcutaneous injection. Zentner et al., supra; Jeong, B.; Bae, Y. H.; Kim, S. W. *J. Controlled Release* 2000, 63, 155-163; Duvvuri, S.; Janoria, K. G.; Mitra, A. K. *J. Controlled Release* 2005, 108, (2-3), 282-293. Thermogelling polymers composed of PEG and PLGA blocks have also been used for delivery of cells and genes as well as proteins. Zentner et al., supra; Li et al., supra.

Based on previous work, thermogelling polymers hold great promise for their biomedical applications. However, new thermogelling polymers, methods of making, and methods of use are needed to broaden the scope of drugs, proteins, cells, and genes that may be delivered.

In view of the foregoing, it will be appreciated that providing aliphatically modified biodegradable thermogelling polymers, methods of making, and methods of use would be significant advancements in the art.

BRIEF SUMMARY OF THE INVENTION

An illustrative embodiment of the present invention comprises a composition of matter comprising an aliphatically modified poly(lactic-co-ε-caprolactone)-poly(ethylene glycol)-poly(lactic-co-ε-caprolactone).

Another illustrative embodiment of the invention comprises a composition of matter comprising an aliphatically modified poly(lactic-co-ε-caprolactone)-poly(ethylene glycol)-poly(lactic-co-ε-caprolactone) made by a method comprising bonding an aliphatic hydrocarbon to poly(lactic-co-ε-caprolactone)-poly(ethylene glycol)-poly(lactic-co-ε-caprolactone).

Another illustrative composition of matter comprises a composition of matter comprising an aliphatically modified poly(lactic-co-ε-caprolactone)-poly(ethylene glycol)-poly(lactic-co-ε-caprolactone) made by a method comprising reacting an aliphatic acid chloride with poly(lactic-co-ε-caprolactone)-poly(ethylene glycol)-poly(lactic-co-ε-caprolactone). Typically, the aliphatic acid chloride comprises a carbon chain of 3 to 18 carbons and, more typically, 6 to 17 carbons.

Still another illustrative embodiment of the invention comprises a composition of matter comprising a mixture of a thermogelling amount of an aliphatically modified poly(lactic-co-ε-caprolactone)-poly(ethylene glycol)-poly(lactic-co-ε-caprolactone) and an effective amount of a drug, cell, protein, or gene.

Yet another illustrative embodiment of the invention comprises a method of making a thermogelling polymer comprising reacting an aliphatic acid chloride with poly(lactic-co-ε-caprolactone)-poly(ethylene glycol)-poly(lactic-co-ε-caprolactone).

Another illustrative embodiment of the invention comprises a method of using a thermogelling polymer comprising injecting a warm-blooded individual with a composition of matter comprising a mixture of a thermogelling amount of an aliphatically modified poly(lactic-co-ε-caprolactone)-poly(ethylene glycol)-poly(lactic-co-ε-caprolactone) and an effective amount of a drug, cell, protein, or gene.

Another illustrative embodiment of the invention comprises a composition comprising poly(lactic-co-ε-caprolactone)-poly(ethylene glycol)-poly(lactic-co-ε-caprolactone) covalently bonded to at least one aliphatic hydrocarbon. Typically, the aliphatic hydrocarbon comprises 3 to 18 carbons and, more typically, 6 to 17 carbons. Illustrative compositions include poly(lactic-co-ε-caprolactone)-poly(ethylene glycol)-poly(lactic-co-ε-caprolactone) hexanoate and poly(lactic-co-ε-caprolactone)-poly(ethylene glycol)-poly(lactic-co-ε-caprolactone) laurate.

Still another illustrative embodiment of the invention comprises a composition comprising a mixture of an effective amount of a drug and a thermogelling amount of poly(lactic-co-ε-caprolactone)-poly(ethylene glycol)-poly(lactic-co-ε-caprolactone) covalently bonded to an aliphatic hydrocarbon.

Yet another illustrative embodiment of the invention comprises a method of forming a depot for time release of a drug, the method comprising injecting a warm-blooded individual with a composition of matter comprising an effective amount of the drug and a mixture of a thermogelling amount of poly(lactic-co-ε-caprolactone)-poly(ethylene glycol)-poly(lactic-co-ε-caprolactone) covalently bonded to an aliphatic hydrocarbon.

DETAILED DESCRIPTION

Before the present aliphatically modified biodegradable block copolymers and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a composition of matter containing "a drug" includes a mixture of two or more drugs, reference to "an aliphatic group" includes reference to one or more of such aliphatic groups, and reference to "a polymer" includes reference to a mixture of two or more polymers.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

As used herein, "PEG" means polyethylene glycol; "PLGA" means poly(lactide-co-glycolide); and "PLLACL" means a copolymer of L-lactic acid and ε-caprolactone or poly-(L-lactic-co-ε-caprolactone).

As used herein, "thermogelling" means that the polymers according to the present invention undergo a sol-to-gel phase transition upon an increase of temperature at an effective concentration.

As used herein, "thermoreversible" means that a gel undergoes a gel-to-sol phase transition upon a decrease of temperature.

As used herein, the term "drug" or any other similar term means any chemical or biological material or compound suitable for administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. Such substances include broad classes of compounds normally delivered into the body. In general, these substances include but are not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

As used herein, "effective amount" means an amount of a drug or pharmacologically active agent that is nontoxic but sufficient to provide the desired local or systemic effect and performance at a reasonable benefit/risk ratio attending any medical treatment.

In an illustrative embodiment of the present invention, a polymer was synthesized that possesses thermogelling properties on the basis of aliphatic modification of biodegradable tri-block copolymers. The hypothesis relating to the polymer was that partial or complete replacement of biodegradable hydrophobic blocks with aliphatic hydrocarbons would be effective in balancing the hydrophilicity/hydrophobicity of a PEG-based block copolymer, which would result in easy modulation of gelling properties of the polymer. It was also a goal to synthesize thermogelling polymers that, once gelled, would degrade in a modulated manner. It is believed that synthesis of thermogelling polymers from aliphatically modified biodegradable tri-block copolymers has never before been reported.

Biodegradable thermogelling polymers have been considered suitable for drug delivery applications due, at least in part, to the ease of formulating injectable depot systems. For simple control of molecular properties to obtain thermosensitive polymers, aliphatic modification of biodegradable tri-block copolymers was carried out. Tri-block copolymers were synthesized from PEG, lactide, and caprolactone. The synthesized polymers did not possess the thermogelling property without aliphatic modification. However, after simple modification with hexyl or lauryl groups, for example, wherein the carbon chains are 6 and 12 carbons in length, respectively, the modified block copolymers underwent thermal gelation upon a temperature rise to body temperature. Physical and thermal properties of the aliphatically modified tri-block copolymers were dependent on polymer concentration and the number of attached aliphatic groups. When the aliphatically modified polymer solutions were injected into rats at a concentration of 20% (w/w), polymeric gel depots were immediately formed. The polymeric gel depots maintained integrity for at least two weeks. With these results, aliphatic modification can be considered as an effective means of controlling the balance of hydrophobicity/hydrophilicity of biodegradable block copolymers for the synthesis of thermogelling polymers.

Polymer Synthesis and Modification

EXAMPLE 1

Figure 1:
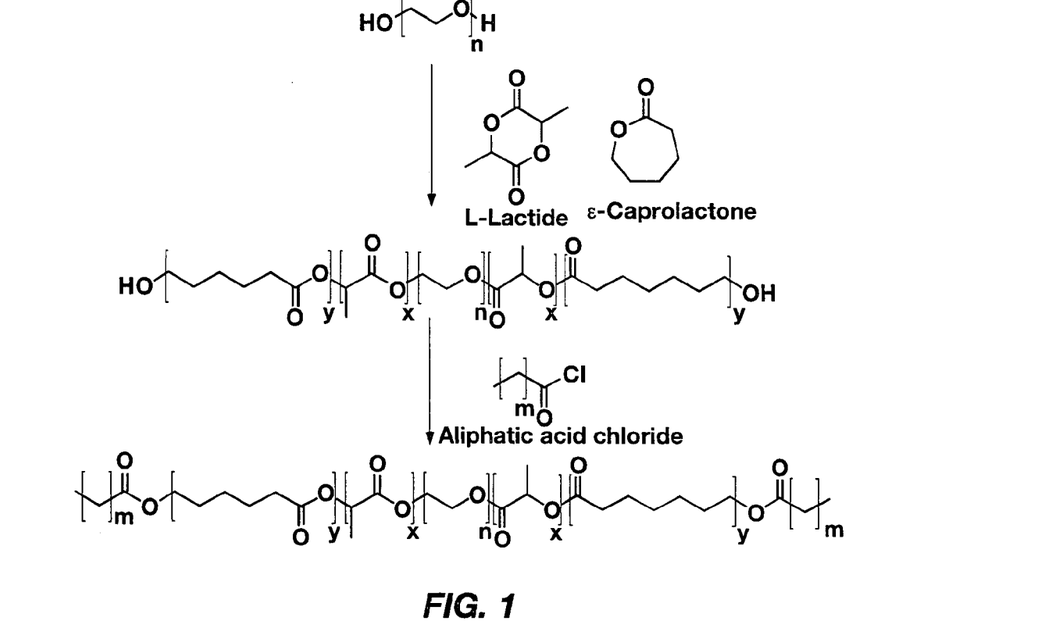
FIG. 1 shows a reaction scheme for the synthesis of PLLACL-PEG-PLLACL and its modification by reaction with an aliphatic acid chloride; m=5 for hexyl, m=11 for lauryl.
Figure 2A:
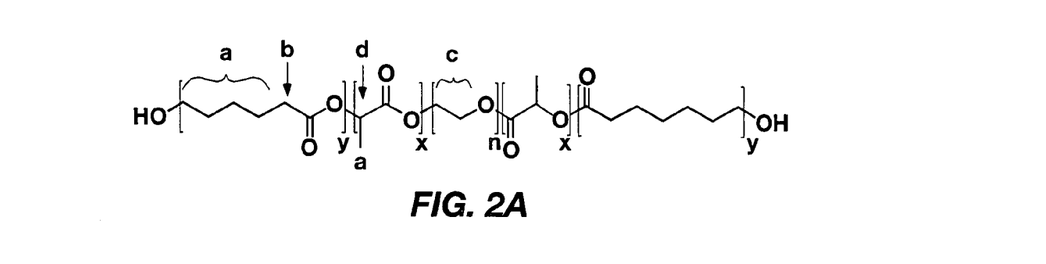
FIGS. 2A-B show structures of PLLACL-PEG-PLLACL and aliphatically modified PLLACL-PEG-PLLACL, respectively, with reference letters a-f showing the structures corresponding to peaks in FIGS. 2C-E.
Figure 2B:
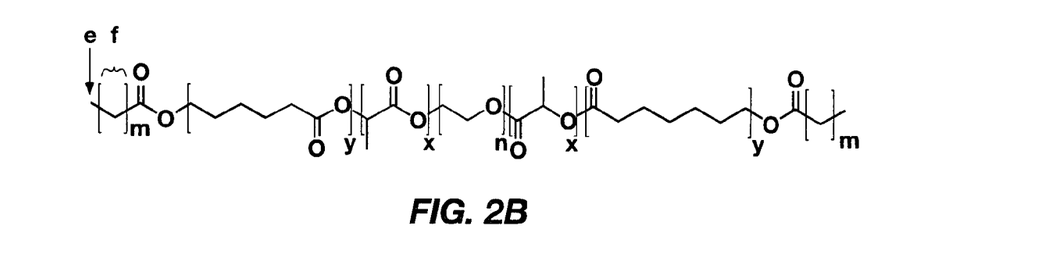
Figure 2C:
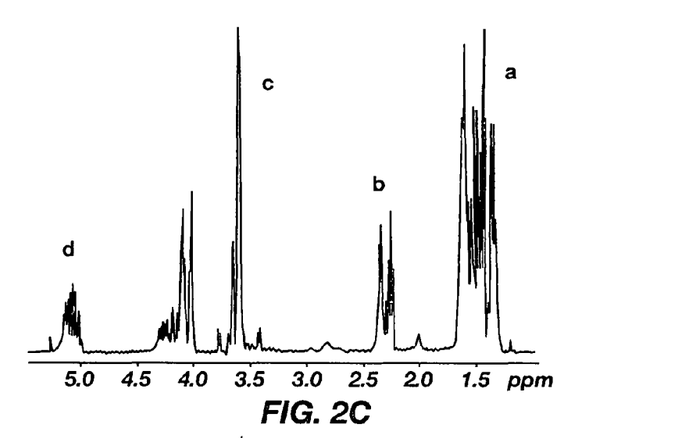
FIGS. 2C-E show NMR spectra of (C) PLLACL-PEG-PLLACL, (D) PLLACL-PEG-PLLACL hexanoate, and (E) PLLACL-PEG-PLLACL laurate in $CDCL_3$.
Figure 2D:
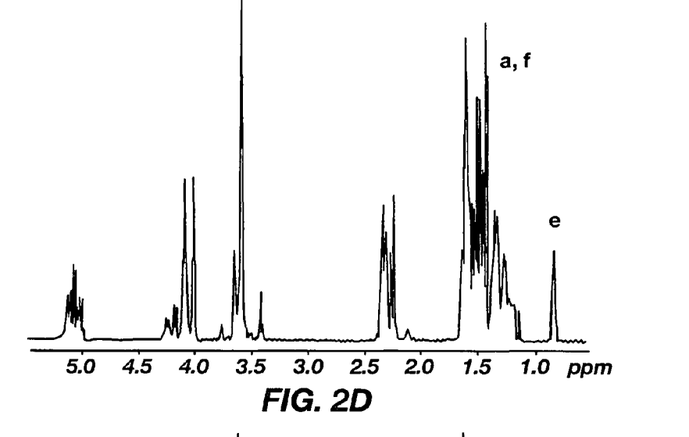
Figure 2E:
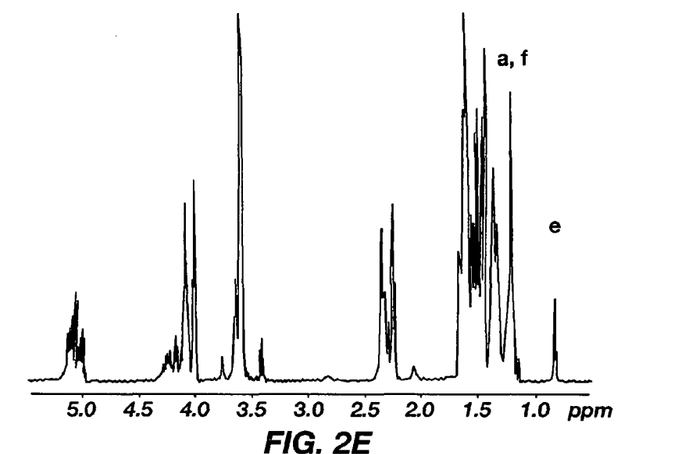

An illustrative scheme for synthesis of biodegradable PLLACL-PEG-PLLACL and its modification is shown in FIG. 1. Fifty grams of PEG (MW 1500, Aldrich Chemical Co., Milwaukee, Wis.) was charged into a 500 mL three-necked round bottomed flask with 300 mL of anhydrous toluene (Aldrich). The PEG was dried by azeotropic distillation by distilling off 120 mL of toluene. After adding 30 g of L-lactide (Boehringer Ingelheim Chemicals, Inc., Petersburg, Va.) and 30 g of ε-caprolactone (Aldrich) into the flask under nitrogen purging, another 100 mL of toluene was distilled off to dry the added monomers. The temperature of the monomer mixture was cooled to 80° C. Next, 500 μL of stannous octoate (Aldrich) was added to the reaction mixture through a 1 mL disposable syringe. The reaction mixture was then refluxed overnight to complete polymerization. Upon completion of polymerization, the cooled reaction mixture was precipitated into an excess amount of anhydrous diethyl ether (reagent grade). The precipitated tri-block copolymer was rinsed twice with diethyl ether. Purified polymer was finally obtained after evaporation of residual solvent with a rotary evaporator. The molecular weight of synthesized polymer was determined to be 3050 by $H^1$ NMR spectroscopy.

Next, 30 g of PLLACL-PEG-PLLACL (9.84 mmole) was dried in a 250-mL three-necked round bottomed flask by azeotropic distillation using 150 mL of anhydrous toluene. The dried tri-block copolymer was cooled to room temperature and dissolved in 100 mL of anhydrous methylene chloride (Aldrich). After mixing triethylamine with the polymer solution, an equimolar amount of lauroyl chloride (Aldrich) was slowly added to the polymer solution in an ice bath. A molar ratio of lauroyl chloride to triethylamine of 1:1.2 was used for the modification. The mixture was reacted overnight at room temperature. Upon completion of the reaction, the aliphatically modified tri-block copolymer was purified as follows. First, methylene chloride was distilled off with a rotary evaporator, and the residual aliphatically modified polymer was dissolved in ethyl acetate. After filtering off the triethylamine hydrochloride salt, the polymer solution was concentrated by distilling off the solvent. Next, the concentrated polymer solution was precipitated into an excess amount of diethyl ether to remove toluene and residual triethylamine. Finally, the precipitated polymer was further dried at 70° C. for 2 hr under reduced pressure.

replace hydrophobic biodegradable blocks with hydrophobic aliphatic groups. After screening of various aliphatic groups with carbon lengths ranging from 6 to 17 (data not shown), hexyl (Example 2) and lauryl (Example 1) groups were chosen for the modification of the polymer. For the aliphatic modification of the tri-block copolymer, hexanoyl chloride and lauroyl chloride were used because end hydroxyl groups of the block copolymer can easily react with them to form ester bonds.

Table 1 summarizes the results of the polymer synthesis and aliphatic modification. The molecular weights of the synthesized polymers were determined by NMR. The NMR spectra of PLLACL-PEG-PLLACL and aliphatically modified PLLACL-PEG-PLLACL in FIGS. 2A-E show characteristic peaks of lactide, caprolactone, and PEG at 5.1, 2.3, and 3.6 ppm, respectively.

TABLE 1

Characterization results of PLLACL-PEG-PLLACL and aliphatically modified PLLACL-PEG-PLLACL by NMR

| Polymer | $M_{n, PLLACL}$ | PLLACL/PEG | CL/LA | Degree of modification | $M_{n, polymer}$ | [a]Solubility |
|---|---|---|---|---|---|---|
| PLLACL-PEG-PLLACL | 845 | 1.13 | 1.65 | — | 3190 | Soluble |
| PLLACL-PEG-PLLACL hexanoate I | 845 | 1.13 | 1.51 | 0.96 | 3300 | Soluble |
| PLLACL-PEG-PLLACL hexanoate II | 960 | 1.28 | 1.24 | 1.70 | 3620 | Turbid |
| PLLACL-PEG-PLLACL laurate | 935 | 1.25 | 1.36 | 0.71 | 3510 | Soluble |

[a]At a concentration of 20 w/w % in PBS
$M_{n, PLLACL}$: Number-average molecular weight of PLLACL block
PLLACL/PEG: the ratio of PLLACL to PEG
CL/LA: the ratio of caprolactone to l-lactide
Degree of modification stands for number of aliphatic groups after polymer modification The synthesized biodegradable tri-block copolymer and aliphatically modified tri-block copolymers were characterized by $^1$H nuclear magnetic resonance (NMR) (Varian, Inc., Palo Alto, Calif.).

EXAMPLE 2

The procedure of Example 1 was followed except that the aliphatic modification of PLLACL-PEG-PLLACL was with hexanoyl chloride (Aldrich) instead of lauroyl chloride, and the molar ratio of PLLACL-PEG-PLLACL to hexanoyl chloride was and 1:2.

EXAMPLE 3

Biodegradable tri-block copolymers were synthesized from PEG of molecular weight 1500, L-lactide, and ϵ-caprolactone according to the methods of Examples 1 and 2. The weight ratio of PEG 1500 to L-lactide and ϵ-caprolactone was 1:0.6:0.6 in the synthesis reaction. This weight ratio was selected to obtain biodegradable tri-block copolymers that did not possess thermogelling properties without aliphatic modification. Biodegradable tri-block copolymers usually possess the thermogelling property at a weight ratio of hydrophobic PLGA blocks to hydrophilic PEG block higher than 1.5. Shim et al., supra; Jeong, B.; Bae, Y. H.; Kim, S. W. *Macromolecules* 1999, 32, 7064-7069; Hwang et al., supra; Bae et al., supra. Before polymer synthesis, a ratio of the blocks in the copolymer was carefully selected to be 1.2, at which ratio the resulting copolymer did not undergo the sol-to-gel transition upon a temperature rise. The main strategy to synthesizing the thermogelling polymer was to partially The molecular weight of the synthesized PLLACL-PEG-PLLACL tri-block copolymer was determined to be 3190 by NMR. Interestingly, the molecular weight of the hydrophobic PLLACL block determined from the NMR spectrum of the tri-block copolymer was not significantly different from the theoretically calculated molecular weight, 900, while the ratio of caprolactone to lactide in the PLLACL block showed a noticeable difference. More caprolactone was found in the hydrophobic blocks than was expected from the feed monomer ratio, which was 1.0. The ratio of caprolactone to lactide in the PLLACL blocks ranged from 1.24 to 1.65, which was noticeably higher than the feed monomer ratio. Based on this result, caprolactone seemed to react more easily than lactide in the ring opening polymerization in this polymer synthesis.

The degree of modification, i.e., the number of aliphatic groups in the modified copolymer, was also calculated by NMR. For the determination of the degree of modification, the characteristic $CH_3$ peak at 0.5 ppm was used. Based on the NMR measurements, PLLACL-PEG-PLLACL was modified with one or two hexyl groups or one lauryl group with end hydroxyl groups. Depending on the degree of modification, aliphatically modified PLLACL-PEG-PLLACL showed different physical properties. When PLLACL-PEG-PLLACL hexanoate I and PLLACL-PEG-PLLACL hexanoate II, with respective degrees of modification of 0.96 and 1.70, were dissolved in PBS to achieve a concentration of 20% (w/w), only the PLLACL-PEG-PLLACL hexanoate with fewer aliphatic groups was completely soluble. The PLLACL -PEG-PLLACL modified with hexanoyl chloride at a ratio of 1:2 was partially soluble in PBS and, thus, resulted in a turbid solution. This result indicates that a slight difference in the number of modified aliphatic groups, about one hexyl group, can cause a significant change in solubility of PLLACL-PEG-PLLACL. Similarly, PLLACL-PEG-PLLACL modified with lauroyl chloride at a molar ratio of 1:1, resulting in a degree of modification of 0.71, was completely dissolved in PBS at a concentration of 20% (w/w). Comparing PLLACL-PEG-PLLACL hexanoate II with PLLACL-PEG-PLLACL laurate in Table 1, there has been no noticeable difference in molecular weight, degree of modification, and thus the balance in hydrophobicity/hydrophilicity. Even though they possessed similar molecular characteristics, they showed different physical properties.

Determination of Sol-Gel Transition

EXAMPLE 4

The sol-to-gel transition of the synthesized polymer solutions prepared according to the methods of Examples 1 and 2 was determined by the test tube inversion method, which is well known in the art. Jeong, B.; Bae, Y. H.; Kim, S. W. *Macromolecules* 1999, 32, 7064-7069; Hwang et al., supra; Choi, S.; Baudys, M.; Kim, S. W. *Pharm. Res.* 2004, 21, (5), 821-31; Choi, S. W.; Choi, S. Y.; Jeong, B.; Kim, S. W.; Lee, D. S. *J. Polym. Sci.: Part A: Polym. Chem.* 1999, 37, 2207-2218. Aliphatically modified polymers were dissolved in phosphate buffered saline (PBS) at concentrations of 5, 10, 15, and 20% (w/w). Four-mL glass vials 1.1 cm in diameter were charged with 1 mL of the aliphatically modified PLLACL-PEG-PLLACL solutions. The vials were immersed in a 5° C. water bath and allowed to reach equilibrium. The temperature of the water bath was increased 2° C. every 5 min, and the polymer solutions were observed. The sol-gel transition temperature was defined as the temperature at which a polymer solution did not flow at all when the vial was inverted.

Figure 3:
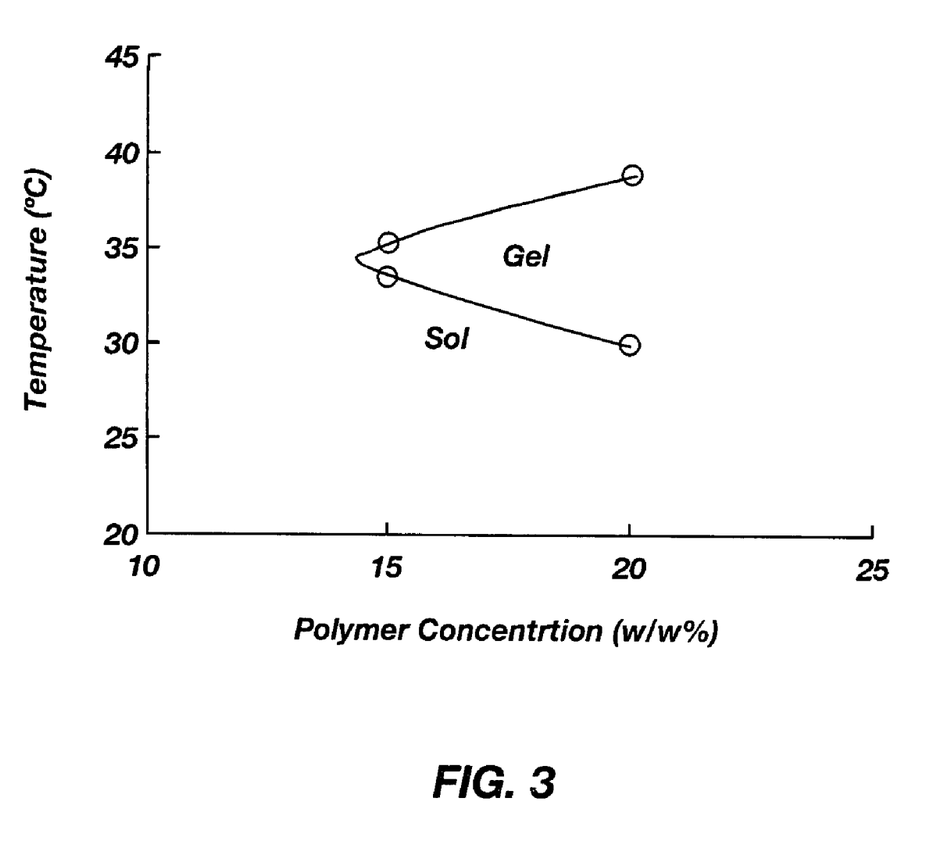
FIG. 3 shows reverse thermal gelation of PLLACL-PEG-PLLACL laurate as a function of polymer concentration.

The sol-to-gel transition of aliphatically modified PLLACL-PEG-PLLACL was studied using PLLACL-PEG-PEG-PLLACL hexanoate I and PLLACL-PEG-PLLACL laurate, both of which are soluble at a concentration of 20% (w/w). The two polymers showed similar thermosensitivity by undergoing the sol-to-gel transition at 30° C. at this concentration. Thermogelling behavior of PLLACL-PEG-PLLACL laurate solution as a function of polymer concentration is shown in FIG. 3. As a matter of fact, the thermogelling of PLLACL-PEG-PLLACL hexanoate I and the thermogelling of PLLACL-PEG-PLLACL laurate were so similar that the two gelation curves almost overlapped. FIG. 3 shows the phase transition of PLLACL-PEG-PLLACL laurate solution as an example. Aliphatically modified PLLACL-PEG-PLLACL needed a polymer concentration of higher than 15% (w/w) for gel formation upon a temperature rise. In this example, four polymer concentrations, 5%, 10%, 15%, and 20% (w/w) in PBS, were used for the investigation of thermogelling of aliphatically modified PLLACL-PEG-PLLACL. Thermal gelation of the aliphatically modified PLLACL-PEG-PLLACL occurred at polymer concentrations of 15% and 20% (w/w). Compared with thermosensitive PLGA-PEG-PLGA tri-block copolymers, aliphatically modified PLLACL-PEG-PLLACL tri-block copolymers needed a higher polymer concentration to undergo thermogelling. This might be due to the limited intercalation of hydrophobic blocks in neighboring micelles because of the unique structure of PLLACL-PEG-PLLACL with a degree of modification of 1 or less. When PLLACL-PEG-PLLACL was modified with aliphatic groups, especially at a degree of modification of 1 or less, the resulting polymer had an ABC structure composed of aliphatically modified PLLACL, PEG, and PLLACL blocks, respectively. In comparison with ABA tri-block copolymers, polymers with the ABC structure might be hindered for micelle formation because of a compositional difference in A and C blocks.

In addition, as polymer concentration increased from 15% to 20% (w/w), the gelation temperature of PLLACL-PEG-PLLACL laurate was lowered by 4° C. The gelation temperature of the polymer solution dropped from 34° C. to 30° C. Previous work consistently demonstrated a lowering of gelation temperature with an increase in polymer concentration for PLGA-PEG-PLGA thermogelling polymer solutions. Gelation temperature of aliphatically modified PLLACL-PEG-PLLACL synthesized from PEG 1500 was comparable to that of PLGA-PEG-PLGA synthesized from PEG 1500. Thermogelling PLGA-PEG-PLGA synthesized from PEG 1500 usually underwent thermal gelation at around 28° C. The aliphatically modified PLLACL-PEG-PLLACL will exist as gel inside a body at a concentration of 20% (w/w). Considering a narrow temperature range from 30 to 39° C. in which the aliphatically modified PLLACL-PEG-PLLACL solution at a concentration of 20% (w/w) exists as gel, the polymer solution easily expels bulk water at body temperature. As shown in FIG. 3, there is a slight temperature difference between body temperature and the temperature at which PLLACL-PEG-PLLACL laurate underwent phase separation. After spontaneous exclusion of water, the polymeric gel gets denser and its stability is improved. This self-condensing thermogelling polymer is suitable for drug delivery applications because the polymeric gel can extend drug release after being condensed.

In Vivo Depot Formation and Gel Integrity

EXAMPLE 5

The aqueous solutions of aliphatically modified thermogelling polymers were injected into the dorsal area of rats at a concentration of 20% (w/w) in PBS. After being loaded into 1 mL syringes, the polymer solutions were injected through 25 G needles in a decisive manner. Five Sprague-Dawley rats weighing 300 g were used for each polymer formulation. After injection of polymer solutions, rats were sacrificed at days 1, 4, 7, 12, and 14. Skin was carefully incised, and attached fat and tissues were carefully removed from polymeric depots. The polymer depots were observed and images of depots were taken with a digital camera (Nikon).

Figure 4A:
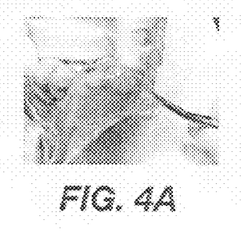
FIGS. 4A-J show in vivo depot formation from (FIGS. 4A, 4C, 4E, 4G, 4I) PLLACL-PEG-PLLACL hexanoate I and (FIGS. 4B, 4D, 4F, 4H, 4J) PLLACL-PEG-PLLACL laurate at a concentration of 20% (w/w). After injections of polymer solutions, polymeric gel depots were observed at 30 minutes (FIGS. 4A-B) and days 4 (FIGS. 4C-D), 7 (FIGS. 4E-F), 12 (FIGS. 4G-H), and 14 (FIGS. 4I-J).
Figure 4B:
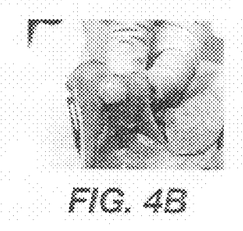
Figure 4C:
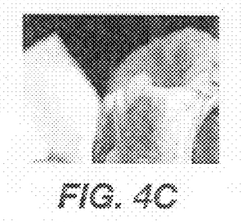
Figure 4D:
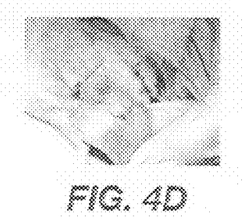
Figure 4E:
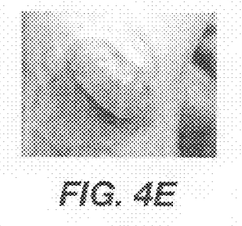
Figure 4F:
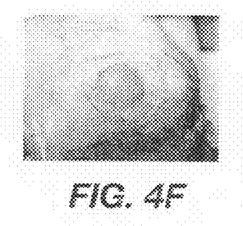
Figure 4G:
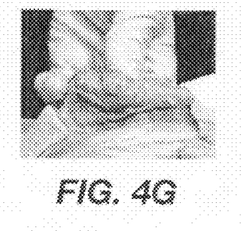
Figure 4H:
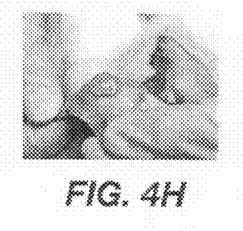
Figure 4I:
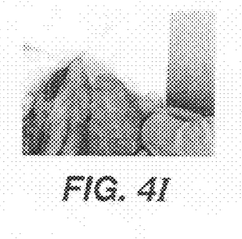
Figure 4J:
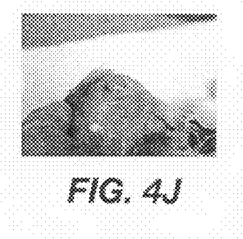

In an animal study to observe in vivo gel formation of aliphatically modified PLLACL-PEG-PLLACL and integrity of the gel, PLLACL-PEG-PLLACL hexanoate I and PLLACL-PEG-PLLACL laurate solutions were subcutaneously injected into rats at a concentration of 20% (w/w). At this concentration, the polymer solutions were easily delivered through 25 G needles. The polymer solutions immediately formed depots, which are shown in FIGS. 4A-B. The gels formed from the aliphatically modified block copolymers were transparent and well defined. The depots from the thermogelling polymers lasted for at least 2 weeks, as shown in FIGS. 4C-J. Within the two weeks, any noticeable development of acute toxicity, such as inflammation and tissue necrosis, was not observed. Inside the depots, dense polymeric gels were observed, which indicated resilient depot formation through water exclusion. The dense gel maintained its integrity up to 12 days. Even after 2 weeks, polymeric gel was observed, although the size of the depot was noticeably reduced because of polymer degradation. Considering these in vivo results, aliphatically modified PLLACL-PEG-PLLACL can be useful for the delivery of therapeutic drugs for 2 weeks or longer.

It is very interesting to note that a slight change in molecular structure of a tri-block biodegradable copolymer induced a dramatic change in a physical property of the polymer. PLLACL-PEG-PLLACL that did not possess the thermogelling property became a thermogelling polymer after a single modification with a hexyl or lauryl group. In addition, this polymer can find applications as injectable drug delivery vehicles for sensitive biological therapeutics, as well as small molecular drugs.

EXAMPLE 6

Prophetic example. The procedure of Example 5 is followed except that a drug is mixed with the polymer solutions prior to injection. The mixture of drug and polymer is then injected into the warm-blooded individual. A drug-containing depot is formed by thermal gelation as the temperature of the mixture rises. The drug is released from the depot over time, probably due to both diffusion and polymer degradation.

The subject matter claimed is:

1. A composition of matter comprising poly(lactic-co-ε-caprolactone)-poly(ethylene glycol)-poly(lactic-co-ε-caprolactone) covalently bonded to at least one aliphatic hydrocarbon.

2. The composition of matter of claim 1 wherein the aliphatic hydrocarbon comprises 3 to 18 carbons.

3. The composition of matter of claim 1 wherein the aliphatic hydrocarbon comprises 6 to 17 carbons.

4. The composition of matter of claim 1 wherein the aliphatic hydrocarbon comprises 6 carbons.

5. The composition of matter of claim 1 wherein the aliphatic hydrocarbon comprises 12 carbons.

6. A composition of matter comprising a mixture of an effective amount of a drug and a thermogelling amount of poly(lactic-co-ε-caprolactone)-poly(ethylene glycol)-poly(lactic-co-ε-caprolactone) covalently bonded to an aliphatic hydrocarbon.

7. The composition of matter of claim 6 wherein the aliphatic hydrocarbon comprises 3 to 18 carbons.

8. The composition of matter of claim 6 wherein the aliphatic hydrocarbon comprises 6 to 17 carbons.

9. The composition of matter of claim 6 wherein the aliphatic hydrocarbon comprises 6 carbons.

10. The composition of matter of claim 6 wherein the aliphatic hydrocarbon comprises 12 carbons.

11. The composition of matter of claim 6 wherein the poly(lactic-co-ε-caprolactone)-poly(ethylene glycol)-poly(lactic-co-ε-caprolactone) covalently bonded to an aliphatic hydrocarbon comprises poly(lactic-co-ε-caprolactone)-poly(ethylene glycol)-poly(lactic-co-ε-caprolactone) hexanoate.

12. The composition of matter of claim 6 wherein the poly(lactic-co-ε-caprolactone)-poly(ethylene glycol)-poly(lactic-co-ε-caprolactone) covalently bonded to an aliphatic hydrocarbon comprises poly(lactic-co-ε-caprolactone)-poly(ethylene glycol)-poly(lactic-co-ε-caprolactone) laurate.

13. A method of forming a depot for time release of a drug, the method comprising injecting a warm-blooded individual with a composition of matter comprising a mixture of an effective amount of a drug and a thermogelling amount of poly(lactic-co-ε-caprolactone)-poly(ethylene glycol)-poly(lactic-co-ε-caprolactone) covalently bonded to an aliphatic hydrocarbon.

14. The method of claim 13 wherein the aliphatic hydrocarbon comprises 3 to 18 carbons.

15. The method of claim 13 wherein the aliphatic hydrocarbon comprises 6 to 17 carbons.

16. The method of claim 13 wherein the aliphatic hydrocarbon comprises 6 carbons.

17. The method of claim 13 wherein the aliphatic hydrocarbon comprises 12 carbons.

18. The method of claim 13 wherein the poly(lactic-co-ε-caprolactone)-poly(ethylene glycol)-poly(lactic-co-ε-caprolactone) covalently bonded to an aliphatic hydrocarbon comprises poly(lactic-co-ε-caprolactone)-poly(ethylene glycol)-poly(lactic-co-ε-caprolactone) hexanoate.

19. The method of claim 13 wherein the poly(lactic-co-ε-caprolactone)-poly(ethylene glycol)-poly(lactic-co-ε-caprolactone) covalently bonded to an aliphatic hydrocarbon comprises poly(lactic-co-ε-caprolactone)-poly(ethylene glycol)-poly(lactic-co-ε-caprolactone) laurate.

* * * * *